United States Patent [19]

Halikas

[11] Patent Number: 5,028,611

[45] Date of Patent: Jul. 2, 1991

[54] TREATMENT FOR COCAINE USE

[75] Inventor: James A. Halikas, North Oaks, Minn.

[73] Assignee: The Regents of the University of Minnesota, Minneapolis, Minn.

[21] Appl. No.: 373,385

[22] Filed: Jun. 29, 1989

[51] Int. Cl.⁵ ............................................. A61K 31/435
[52] U.S. Cl. ..................................... 514/277; 514/812
[58] Field of Search ................................ 514/812, 277

Primary Examiner—Stanley J. Friedman
Attorney, Agent, or Firm—Vidas & Arrett

[57] ABSTRACT

The craving for cocaine and use of cocaine among users may be reduced by administration of carbamazepine. Cocaine-usage is effectively treated with the carbamazepine administration.

7 Claims, 2 Drawing Sheets

FIGURE 1

Demographic and Treatment Comparisons

Across the Three Success Groups

|  | Highly Successful n=10 | Partially Successful n=10 | Unsuccessful n=6 |
|---|---|---|---|
| $\bar{x}$ years substance abuse | 12.8 | 15.7 | 24 |
| $\bar{x}$ years cocaine use | 7.1 | 6.2 | 8.8 |
| $\bar{x}$ number past treatments | 3 | 3.3 | 4.2 |
| $\bar{x}$ daily cocaine use | 1.5g/day | 1.28g/day | .92g/day |
| $\bar{x}$ carbamazepine dose | 390mg/day | 310mg/day | --- |
| cocaine use ratio: |  |  |  |
| pretreatment | 69.2 | 76.5 | 80.2 |
| with treatment | 1.2 | 28.8 | 68.1 |
| total days at risk | 1169 | 1292 | 1259 |

TREATMENT FOR COCAINE USE

BACKGROUND OF THE INVENTION

1. Field of the Invention

This invention relates to a method for reducing the use of cocaine in animals, including humans, by the administration of carbamazepine.

2. Description of the Related Art

Treatment for cocaine abuse has been largely ineffective, based on cocaine relapse rates. Depending on the level of habituation or dependence, and prognostic features, i.e. job, marital status, additional psychopathology, etc., upwards of 60–100% of cocaine dependent patients relapse within the first 12 months no matter how high their motivation. For most, this relapse rate is due to an overwhelming "craving" for the drug (Dackis et al, *Arch.Gen.Psychiatry*, 44: 298-9, 1987).

There have been a number of studies in which various pharmacologic agents have been used to treat cocaine dependence: Bromocriptine, bromocriptinedesipramine combination, amantadine, imipramine, L.tyrosine and L.tryptophan in combination, and desipramine. Both amantadine and bromocriptine have been used primarily to treat the cocaine withdrawal syndrome but long-term studies using either have not yet been conducted.

The tricyclic antidepressant, desipramine, has been the most extensively studied of pharmacologic agents. Maintenance with desipramine for 3-4 weeks is required before any significant decrease in craving occurs.

Biological hypotheses regarding cocaine craving have focused on the dopaminergic reward pathways. Two of the more recent theories have suggested that craving is at least in part due to a "down" regulation of the dopamine reward system following chronic cocaine abuse. Instead, the inventor postulates that cocaine craving involves an alternate specific neurophysiological mechanism related to kindling.

The art described in this section is not intended to constitute an admission that any patent, publication or other information referred to herein is "prior art" with respect to this invention, unless specifically designated as such. In addition, this section should not be construed to mean that a search has been made or that no other pertinent information as defined in 37 C.F.R. §1.56(a) exists.

SUMMARY OF THE INVENTION

It has been found that daily administration of carbamazepine will decrease the "craving" for cocaine. It is the craving which makes the habit so difficult to break. Carbamazepine is a chemical compound that has proven highly effective for over twenty years in the treatment of different types of seizure disorders. It is especially effective in treating generalized seizures thought to arise from the limbic system and the temporal lobe.

Cocaine abusers were treated with carbamazepine in doses of 200–600 mg per day. To date, a remarkable response has been noted in those patients who have used carbamazepine regularly. Carbamazepine is begun immediately upon entering the treatment program, whether or not the patient receives any other medications to manage acute withdrawal discomfort.

It has been spontaneously noted and described by all of the 13 patients who have taken carbamazepine, whether for short periods or for extended periods, that the subjective feeling of craving is significantly reduced or, in some, completely absent. This reduction or absence of craving exists even in high risk, high temptation situations, such as being with cocaine addicts who are actively using the substance. Since the cocaine craving in these individuals is normally overwhelming in such situations, this reduction or absence of craving is striking. Blockade of craving and euphoria was noted in two cases who sought to override carbamazepine.

Psychostimulants and psychoactive drugs also cause kindling, the facilitation of neuronal activity. Therefore, carbamazepine may be used to treat abuse of such drugs.

BRIEF DESCRIPTION OF THE DRAWINGS

A detailed description of the invention is hereafter described with specific reference being made to the drawings in which:

FIG. 1 presents demographic, substance abuse history and pattern of cocaine use in a clinical open trial.

DESCRIPTION OF THE PREFERRED EMBODIMENTS

Cocaine Craving

Figure 2A:
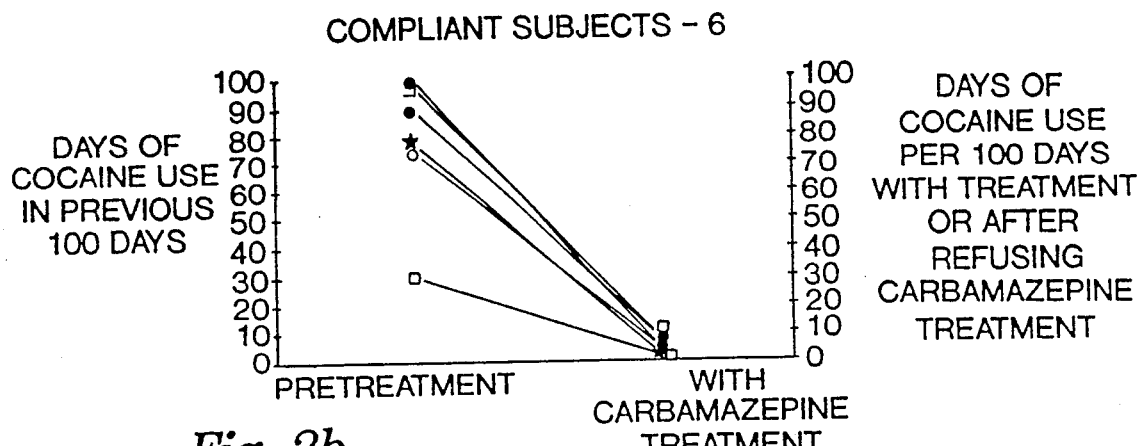
FIG. 2 consists of three graphs numbered 2a, 2b and 2c showing data as to Compliant Subjects, Partially Compliant Subjects and Carbamazepine Refusers, respectively, as patients.

Cocaine craving is a subjective psychological state characterized by an overwhelming urge or compulsion to repeat the drug experience. Intravenous cocaine users describe a profound loss of control, and will frequently self-administer single bolus doses every 10-20 minutes until access to the drug is no longer available. Craving which occurs several weeks into the recovery process can also be extremely intense. This delayed craving seems related to a memory "replay" of the original drug experience, elicited by environmental cues which have become associated with cocaine use. These triggers are endlessly diverse and highly individualized.

The term "kindling" in neurophysiology refers to the progressive facilitation of neuronal firing, in discrete regions of the brain, elicited by temporally spaced exposure to specific pharmacologic or electrical stimuli. When induced pharmacologically, this neuronal firing occurs with progressively lower doses of stimuli. In animals, this firing can increase in magnitude to seizure activity. Tatum and Seevers [*J. Pharmacal. Exp. Ther.*, 36: 401–410, (1929)], over fifty years ago, observed that giving rats, dogs and monkeys the same dose of cocaine, produced increasing psychomotor excitability and eventual lethality. Goddard et al [*Exp. Neurol.* 25: 295 (1969)] demonstrated the electrical kindling phenomenon by delivering fixed daily amounts of electrical stimulation to the region of the amygdala in rats. Previously non-convulsant test animals eventually developed seizures, with a permanent lowering of the seizure threshold.

More recently, pharmacologic kindling has been extensively investigated by Post and Kopanda [*Am. J. Psychiatry*, 133: 627–734 (1976)] using a variety of psychomotor stimulants and anesthetics. Temporally spaced injections more than 24 hours apart of fixed subconvulsive doses of cocaine, elicited major motor seizures as an endpoint in the kindling process, with a variety of mid-stage kindling "behavioral" responses.

Ellinwood and Kilbey [*Animal Model in Pshychiatry & Neurology* Ed: E. Hanin & E. Usdin, N.Y. (1977)] observed mid-stage kindling or "behavioral sensitization" effects of repeated administration of amphetamine, which was labeled reverse tolerance. Animals of all species studied developed specific stereotypy and disruption of learned behavior (mid-stage), before they progressed to major motor seizures (late stage).

In animals, limbic system structures, especially the amygdala and hippocampus, produce prominent seizure and after-discharge activity in response to cocaine administration in adequate doses. This electrical activity may then spread outside the limbic system and be associated with major motor seizures. It should be noted that the hippocampus has been shown to have an "exceedingly low" threshold for seizure activity and to be involved in learning and memory processes.

Post, Kopanda, and Black [Bio. Psychiatry, 11: 403–419 (1976)] demonstrated, in rhesus monkeys, that an individual standard sub-seizure-threshold dose of cocaine, when administered repeatedly over time, intraperitoneally, resulted in the onset of seizures. Once a seizure had been produced, the average number of cocaine doses required to produce a seizure decreased with time. In one of their animals, a single cocaine dose was eventually needed to induce seizure activity.

It has been suggested that in humans the progressive increases in irritability, restlessness, hypervigilance and paranoia associated with chronic high dose cocaine use may be the human correlate of the kindling phenomenon in the animal research paradigm.

Pollock [*Pyschiat. J. Univ. of Ottawa* 10:4, 185–192 (1985)] has summarized the major characteristics of the kindling process. First, the progressive lowering of after-discharge threshold in surrounding neuronal tissue occurs in response to stimuli of physiologic proportion. The kindling response is enhanced when the interval between stimuli is 24 hours or greater. If stimuli are less than two hours apart kindling is significantly delayed. Secondly, Pollock suggests that kindling progresses through stages which can be observed and recorded prior to late-stage kindling which is major motor seizure activity. Specific behavior changes such as stereotypy, and EEG changes correspond to the stepwise progression of mid-stage kindling A third feature of kindling pertains to gradients of neural susceptibility. Certain areas of the brain, amygdala and limbic system structure, are much more sensitive to the kindling phenomenon than are the neocortex, brain stem and cerebellum which are relatively impervious to kindling. A fourth aspect of kindling is related to its sustained effect. Kindled animals appear to have permanent neuronal sensitivity, which is not explained on the basis of toxic metabolites, pharmacokinetic factors or destructive lesions at the tip of the electrode.

CARBAMAZEPINE

Carbamazepine is a clinically useful anti-convulsant which affects temporal lobe dysfunction. In animals, carbamazepine, selectively inhibits early, i.e., developmental, phases of pharmacological kindling induced by local anesthetics. Chronic administration blockades the development of cocaine-kindled seizures in animals. It also blockades the late phases of electrically kindled seizures in animals [Post, *J. Clin Psychiatry*, 49 (Suppl): 4, 1: 35–46 (1988)].

A separate line of research has demonstrated that both carbamazepine and cocaine have significant but apparently often opposite effects on several neurotransmitter systems. In the dopamine system, cocaine causes decreased release of dopamine from the ventromedial mesencephalon, inhibited uptake of dopamine in mesoaccumbens neurons, increased dopamine metabolism in the striatum, and possibly induces dopamine autoreceptor supersensitivity.

Cocaine affects the norepinephrine system by inhibiting the spontaneous firing of locus ceruleus neurons, increasing hypothalamic metabolism, and decreasing norepinephrine synthesis. The serotonin system is affected by inhibited synaptosomal uptake of serotonin, decreased-serotonin concentration in the caudate, decreased serotonin turnover in the brain, and reduced serotonin synthesis (reflected by decreased uptake of tryptophan and decreased tryptophan hydroxylase activity.

Carbamazepine increases dopamine concentration in brain slices and cerebroventricular perfusates, blocks synaptosomal norepinephrine re-uptake, increases the firing rate of locus ceruleus neurons, increases plasma tryptophan, and increases acetylcholine levels in the striatum.

Cocaine-induced, or "kindled", seizures have been documented in animals. A search of the scientific literature has not yielded any reports as yet of human cocaine-kindled seizures. In the course of treatment of cocaine addicts at the University of Minnesota Hospitals, a human example of cocaine-kindled seizures was encountered.

TESTING

Case Report: Human Cocaine-Kindled Seizure Activity

The patient is a 38-year old white male with a lengthy history of cocaine dependence and also opioid dependence for which he is on methadone maintenance. The patient has no history of cranial trauma or personal or family history of seizure disorder or other neurologic disorder. For the past 20 years, except for a two-year prison-induced abstinence, the patient has regularly, but intermittently, used cocaine, almost exclusively by the intravenous (IV) route. He has used up to 5 grams per day. Prior to 1984, the patient had never experienced any seizures while administering intravenous cocaine to himself. In 1984, the patient experienced a seizure-like episode after having used a total of 4–5 grams of cocaine intravenously in 0.2–0.3 gram boluses within a 12-hour period. This seizure episode consisted of clonic activity of both upper extremities and "staring straight ahead. I just couldn't do anything about it," which lasted for an estimated 2–3 minutes without loss of consciousness or sphincter incontinence. Prior to this episode, the first 0.2–0.3 grams of cocaine taken during a session would produce euphoria. This seizure episode greatly disturbed the patient but he found himself essentially powerless in the face of his cocaine dependence.

During the next 12 months the patient discovered that he would experience seizure activity of this type after using a total of 3–4 grams of cocaine over the course of a day. The seizures would frighten him, and he would cease cocaine use. The next morning he would feel compelled by his dependence to use again. A bolus of approximately 0.2 grams of cocaine at that time would, within approximately 30 seconds, produce another seizure episode, this time accompanied by the instant paranoid feeling of having been discovered by law enforcement authorities, and by auditory hallucination, consisting of non-threatening voices. He frequently noticed himself drooling following these seizure episodes. He once waited approximately three days following an IV cocaine-induced seizure episode prior to using cocaine again and still precipitated a seizure on his first injection of an approximately 0.2-0.3 gram bolus.

During the next 2-3 years the patient discovered that it took progressively less total grams of IV cocaine to precipitate a seizure of the type indicated above. In recent months a total of only 0.5 grams could produce a seizure. The extent, character, and magnitude of the seizure has not changed over time, but the patient is unsure whether the duration of each seizure episode has increased.

Since August, 1988, as part of an open label treatment protocol, the patient has received carbamazepine as adjunctive therapy for his cocaine dependence. Although he has taken the medication intermittently, he has had only six days' of cocaine use in 14 weeks. When he takes the carbamazepine, he reports significantly reduced craving. Without the carbamazepine, he reports a return of severe craving for cocaine. Five of the days of cocaine use occurred when he had stopped taking the carbamazepine for several days. The other single day of cocaine use occurred while he was taking arbamazepine.

Over the course of one week, the patient had, without the knowledge or approval of his physician, increased his carbamazepine dose to 900 mg per day. He then used a total of about 3 grams of cocaine IV over a six-hour period in 0.2-0.3 gram boluses. He experienced euphoria, but only after he has used 0.5 grams total over about one-half hour. He denied experiencing a seizure, but did finally experience paranoia after he has used a total of about 1.5 grams over 2-3 hours.

An MRI scan of the patient's brain was negative for any pathology. A sleep-deprived EEG done while the patient was not taking carbamazepine, demonstrated intermittent right temporal lobe focal slowing.

This man has developed cocaine-induced clonic seizures and that they have become progressively more easily initiated at lower and lower cocaine doses because of putative development and spread of "kindling".

Clinical Open Trial

The population: The patients participating in this project to date are cocaine abusers who either spontaneously sought help in the University of Minnesota Chemical Dependency Treatment Program or were referred through the Minneapolis Methadone Maintenance Program after the discovery of cocaine in their urines. Of the 26 subjects treated to date, 14 have also been receiving methadone in the area methadone program. Sixteen patients are male, 10 are female; 15 are white, 11 are black. Their average age is 34 with an age range from 23-57. FIG. 1 summarizes demographic and treatment comparisons.

Substance abuse history: The subjects in this sample are not novice drug users. They have generally been using illegal substances since early in their adolescence (mean age of onset about 17). They have averaged 17 years of substance abuse out of their 34 years of life. They have been using cocaine for an average of 7 years. This group averaged more than 3 past treatment attempts (this excludes detox admissions).

They have been involved in numerous antisocial activities, averaging ten lifetime arrests (9.9) and an average of 17 months in jail over the course of their lifetime. Only one had never been arrested. Half of the group had past cocaine-related arrests, (mean=4). About half of the group had been arrested for violent crimes (mean=4). They could not be characterized as a "YUPPIE" population of recreational cocaine users. Rather, these were all heavily into the world of illicit drug use as a career.

All but 6 of the 26 subjects used their cocaine regularly by the intravenous route. Smoking of cocaine in the form of "crack" also was a common route of administration for about half of the group. On days they used cocaine, they averaged about 1.25-1.50 g. Of those on methadone at the outset, their average methadone dose was 70-75 mg per day.

Quantification of frequency of cocaine use: An attempt has been made to quantify the frequency of cocaine use in this population. Based on personal interview, each patient was asked to recall as carefully as possible the prior 100 days, and to indicate as accurately as possible days of use and days of nonuse. The range for this group of patients was between 30 days and 100 days of use during the prior 100 days. Three of the subjects had used cocaine between 30-50 days in the prior 100 days. All the rest (n=23) had used it on more than 50 days of the prior 100 days. The average number of days of use for the entire group of 26 was about 75 days of use during the prior 100 days, or about $\frac{3}{4}$ of the possible days at risk.

Methodology: Individuals referred to the University of Minnesota Chemical Dependency Treatment Program were evaluated in the usual manner as outpatients. If it was felt that they required hospitalization to begin the rehabilitation process, they were scheduled for admission and entered a 10-14 day inpatient first phase. Promptly on admission, all of these patients were begun on carbamazepine with 200 mg taken within 12 hours of admission, 400 mg by the end of the first full day of hospitalization, and 600 mg per day thereafter, in divided doses. (Only Tegretol brand of carbamazepine was used, because of the more reliable pharmacokinetic profile it has than have the generic brands [Sachdeo and Belendick, *Lancet*, 1:1432 (1987)]. In addition, significantly variable rates and degrees of GI absorption have been noted with generic carbamazepine. Patients could refuse or discontinue the medication at any time. In addition to carbamazepine, six patients, as indicated, were either tried or maintained on other medications at some point (lithium-1, imipramine-1, desipramine-1, amitriptyline-1, doxepin-1, amantadine-1, dilantin-1).

Patients were enrolled in the day hospital cocaine program as soon as possible. Sometimes, this attendance occurred even prior to hospitalization, but at the very least, during the hospitalization they attended these meetings. After discharge, patients were expected to attend the weekly Thursday evening clinic which included medication management for their carbamazepine and for any other medications they might still be taking. Each patient was asked to complete a systematic assessment of craving at each visit [Dackis and Gold, *J. Subst. Abuse Treat.*, 2:139-145 (1985)]. In addition, urine drug screens were obtained every 1-2 weeks on a random basis.

The weekly two hour group therapy session included many components: drug abuse education; relapse prevention strategies including analysis of behavioral chains and sabotaging recovery; the development of coping skills and shared techniques for dealing with situations in a non-drug fashion; a review of the past week including high risk situations; general supportive therapy through the group process; and encouragement to participate in self help groups such as Cocaine Ananonymous outside of the treatment group.

Figure 2B:
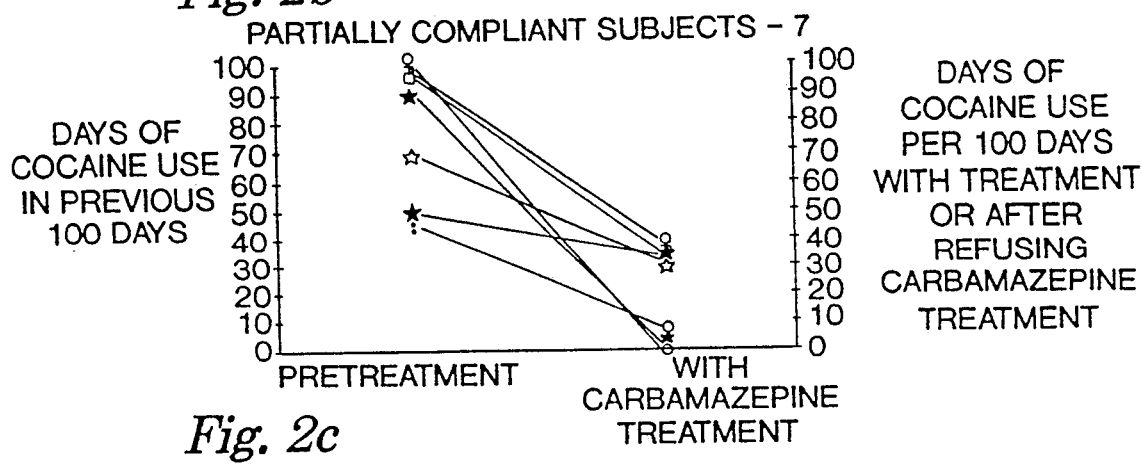
Figure 2C:
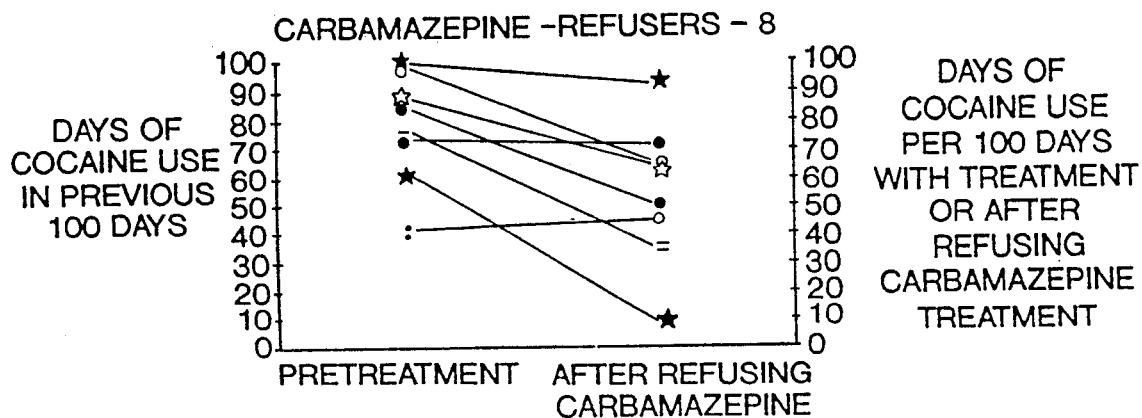

Results: Of the 26 patients offered carbamazepine to date, 6 patients refused it or took it less than 3 days. Of the 20 patients who have taken carbamazepine more than 3 days, 10 have been judged to be at least partial successes, with intermittent use of the carbamazepine and progressive periods of cocaine abstinence during its use. Ten patients have had clear success, with abstinence ranging from 1–8 months, and associated with regular carbamazepine ingestion. Data on these patients is shown in FIG. 2.

The 10 patients with apparent clear success averaged a somewhat higher dose of carbamazepine, with a mean and median both of 350 mg daily. The intermittent use group had a mean and median of 300 mg per day on days when they took it.

The ratio of cocaine use per 100 days during the treatment interval for each group was derived in an effort to assess comparability of results. The 10 successful patients, as of Feb. 22, 1989, had decreased their use from 69 days per 100 days pretreatment to 1.2 days per 100 days during carbamazepine treatment, with a total of 1,169 days at risk for that group.

The 10 patients judged to have an intermediate success had a reduction from 76.5 days pretreatment to 28.8 days post initiation of treatment with a total of 1,292 days at risk for the group. They used carbamazepine on approximately 40–45% of the days in which they had it available.

The carbamazepine refuser group had a total of 1,159 days at risk after the initiation of their participation in the program. They experienced minimal change in their use, from 80.2 days per 100 days at risk to 68.1 days per 100 days at risk after initial opportunity to utilize carbamazepine.

As might be expected, the successful group was more likely to attend the weekly group sessions, averaging an attendance rate of about two-thirds of the time. There was an average of eight urine analyses for cocaine obtained for each of these subjects, with only one subject having a positive urine on one occasion.

The intermediate success group had an attendance rate of about 40%. They averaged just under five urine analyses per person and had almost two positive urines per person.

The carbamazepine-refuser group had the poorest attendance record, appearing for groups about one-third of the time. Accordingly, they had the fewest number of urine analyses performed, averaging somewhat more than two per person, with virtually all of them being positive for cocaine.

All of the subjects who took carbamazepine, whether intermittently or regularly, agreed that cocaine craving was significantly reduced even while in high risk situations such as observing others using or preparing cocaine. This reduction in craving began almost with the first dose, and certainly within 72 hours significant reduction or disappearance of craving subjectively was noted.

The methadone users consistently reported the appearance of early opiate withdrawal symptoms (18–24 hours post methadone dose). Based on the fact that carbamazepine will induce liver enzymes which metabolize methadone this clinical observation was likely accurate. The need to increase the daily doze of methadone by 10–15% became readily apparent.

Conclusions: Open Clinical Trial

In this limited open clinical trial, compliance with carbamazepine therapy indeed was associated with significant reduction in the frequency of cocaine use. Further, patients taking carbamazepine reported subjective reduction in the frequency, duration, and intensity of cocaine craving. Anecdotally, three subjects who used cocaine while taking carbamazepine reported a reduced cocaine effect, a "blockade" effect.

Carbamazepine induces hepatic microsomal enzymes resulting in a decrease in the half-life of methadone hydrochloride. Methadone maintenance patients using cocaine who are treated with carbamazepine may require an increase in their methadone dose.

Abstinence from cocaine was associated with compliance with carbamazepine but not other sociodemographic variables or drug use history.

Example of Carbamazepine-Blockade of Cocaine Effects

The patient is a 29 year old single white male who was free basing cocaine in amounts ranging from 2 grams to ½ ounce daily for 30 days prior to his inpatient admission. Four weeks following initiation of carbamazepine therapy the patient had an argument with his wife and began drinking. He then purchased an "eight ball" (3.5 grams) of cocaine hydrochloride powder and converted it to the free base form which he smoked. After 1.5 grams was consumed in less than an hour, he found that he did not experience his usual cocaine euphoria. He repeated the same amount the next day and on a subsequent occasion with identical results, and was convinced that carbamazepine blocked his usual cocaine effect. He subsequently stopped carbamazepine for two days and repeated the free base experience, smoking 1.5–2 grams rapidly. He reported appearance of the original cocaine euphoria while off the carbamazepine.

Methadone Maintenance Patients

The cocaine epidemic of the past decade is undermining the efficacy of methadone maintenance treatment. Patients who had stabilized on methadone and had given up intravenous heroin use are now back in the street-drug subculture, with progressive loss of control to cocaine. Intravenous cocaine use has emerged as the predominant route of administration for this group.

In an open clinical trial, 11 methadone maintenance patients dually addicted to cocaine were offered carbamazepine as a pharmacological adjunct for the treatment of cocaine dependence. All 11 were intravenous cocaine users, who average 70/100 cocaine using days prior to referral to the cocaine clinic at the University of Minnesota. Patients were referred from both area programs. The average amount of cocaine use was 3.5 grams weekly; average cocaine use history was six years; associated history of illicit drug involvement was 16 years. Of the 11 patients, three were female; of the eight males, three were black. Their average age was 38, average lifetime drug related arrests was 12, and they averaged four previous treatment attempts.

Four patients began carbamazepine treatment as inpatients on the chemical dependency unit. Initial carbamazepine doses were 200 mg given two to three times daily. On the second day following initiation of carbamazepine therapy, two patients simultaneously began to complain of restlessness and insomnia which was progressive through the night, and was relieved by the next morning dose of methodone. The patients decided that the methadone dose they were receiving in the hospital was not "holding". The symptoms of global apprehensiveness and restlessness again appeared 12-16 hours following the morning methadone dose, and a third patient began complaining of "the methadone wearing off". Opiate withdrawal rating criteria failed to clearly document objective measures of methadone withdrawal. The re-emergence of the same nocturnal symptoms on the fourth hospital night, relieved by the morning methadone dose, suggested one of two possibilities. Either the patients had conspired to try to manipulate methadone dosage increase, or carbamazepine had somehow affected the steady-state equilibrium of the methadone.

Methadone serum trough levels were obtained before the morning dose which were found to be consistently below 800 ng/ml. Subsequently, with the approval of the referring methodone program, small increases in methadone (10 mg.) were recommended, which eliminated the nocturnal symptoms.

A two-hour weekly support group was provided for the cocaine patients. This included cocaine education, relapse prevention planning, peer support, and a review of recovery principles. Compliance on the carbamazepine was quite poor following the groups' discussions regarding the possible effect on methadone metabolism of carbamazepine. Although several patients described the craving reduction effect of carbamazepine, many methadone maintenance patients were more concerned about "having the methadone wear off".

Of the original 11 patients, six completed the program, and continued on carbamazepine for more than 45 days. Four discontinued the medication between 7 and 45. One was a non-starter (less than seven days on the carbamazepine).

The methadone maintenance patients who took carbamazepine reduced their frequency of cocaine use from 70/100 days pre-treatment to 26/100 days with carbamazepine treatment. The other five patients did not have a significant change in the frequency of cocaine use.

Subsequent methadone serum through levels taken before and after initiation of carbamazepine therapy further supported the clinical observation that methadone trough levels are reduced by carbamazepine.

The use of carbamazepine in the methadone maintenance population must be approached with caution. However, if serum trough levels are obtained before and after, methadone dose adjustment can correct the initial effects of carbamazepine on methadone steady-state.

Kindling Hypothesis of Cocaine Craving

In summary, in animals, carbamazepine blocks early development of pharmacologically-induced kindling and cocaine kindled seizure activity. Craving has been reduced or eliminated in 13 carbamazepine treated cocaine patients to date. There appear to be several "behavioral" manifestations of developing kindling in animals short of major motor seizures already identified, including stereotypy, disrupted learning, and reverse tolerance. In humans, too, there may be many manifestations of developing kindling. It is hypothesized on the basis of clinical observations of reduction of craving in this population that cocaine craving may be the psychological and behavioral manifestation of the kindling or neuronal supersensitivity seen in animal studies. It is hypothesized that the changes brought about by cocaine in the limbic system, specifically the kindling noted in the amygdala and the hippocampus, and the decreased firing rate of locus ceruleus neurons, is also present in humans, although this has not as yet been demonstrated. It is contended that this kindling in humans is the basis of the behavior which is termed "craving." This cocaine craving is reduced or reversed at both a neurophysiological level and at a behavioral level with carbamazepine. The behavioral conditioning principles of intermittent reinforcement and imprinting may be related to these same neurophysiological events. In cocaine dependent patients, long-term or delayed craving for cocaine may be the behavioral manifestation of kindling. This is named the Kindling Hypothesis of Cocaine Craving.

OTHER PSYCHOSTIMULANTS AND PSYCHOACTIVE COMPOUNDS

In addition to cocaine, over the last 60 years, the kindling phenomenon in animals has been documented with a variety of other psychostimulants, amphetamines, local anesthetics, and electrical stimulation. Although comparable work has not yet been done with phencyclidine (PCP) or lysergic acid diethylamide (LSD), it is a reasonable extension of kindling hypothesis to expect that they also will cause facilitation of neuronal activity. This would account for the clinical observation in the 1960's and 1970's of "flashbacks" with LSD, and the observation in the 1970's and 1980's of residual mental changes of a semi-permanent nature in patients who had abused PCP repeatedly. Other drugs which have either been demonstrated to cause kindling, or could be expected to cause kindling based on this hypothesis include:

Methamphetamine
Methylene dioxymethamphetamine (MDMA)
Amphetamine
D amphetamine
Methylphenidate
DL phenylpropanolamine (PPA)
Procaine
Lidocaine
Methedrine
Desoxyn
Cocaine
Freebase
Crack On the basis of the consistency of the hypothesis and clinical observations to date, it is expected that carbamazepine will provide an effective treatment to reduce or eliminate the use of psychostimulants and psychoactive agents as well as cocaine.

KINDLING RELATED DISORDERS

It has been demonstrated that animal and human behavior can be taught with relatively few trials if the organism is ready for the new experience, and trained at the right moment in its growth and development. In behavioral psychology this type of learning is called "imprinting". In humans, there has long been a clinical observation that certain traumatic psychological or physical events may leave a lasting, recurrent upsetting memory. While this has been most obvious with Vietnam veterans, it is also seen with adults who have been physically or sexually abused in childhood. This has now been labeled, clinically, the Post-Traumatic Stress Disorder (PTSD). Some patients with this syndrome have recurring patterns of dreams and nightmares, violent outbursts in response to unpredicted environmental triggers, and a high propensity to alcohol abuse and depression. There is at least one clinical study indicating that carbamazepine is useful in alleviating the symptoms of Post-Traumatic Stress Disorder. This would be consistent with the hypothesis regarding the development of kindling in these patients. In this case, not on the basis of an external chemical introduced into the creature, but rather on the basis of a sudden, excessive, emotionally traumatic sensory overload which is imprinted electrically in the same areas of the limbic system as are other forms of kindling. In short, a plausible extension of the hypothesis is that traumatic events may cause the development of a similar facilitation of neural activity which could be treated with carbamazepine.

While this invention may be embodied in many different forms, there are shown in the drawings and described in detail herein specific preferred embodiments of the invention. The present disclosure is an exemplification of the principles of the invention and is not intended to limit the invention to the particular embodiments illustrated.

This completes the description of the preferred and alternate embodiments of the invention. Those skilled in the art may recognize other equivalents to the specific embodiment described herein which equivalents are intended to be encompassed by the claims attached hereto.

What is claimed is:

1. A method for reducing the use of psychostimulants and psychoactive compounds which cause kindling in animals, which method comprises orally administering to an animal in need an effective amount of carbamazepine or a pharmaceutically acceptable acid addition salt thereof.

2. The method of claim 1 wherein said psychostimulants and psychoactive compounds are selected from the group consisting of phencyclidine (PCP), lysergic acid diethylamide (LSD), methamphetamine, methylene dioxymethamphetamine (MDMA), amphetamine, D amphetamine, methylphenidate, DL phenylpropanolamine (PPA), Procaine, Lidocaine, Methedrine, Desoxyn, cocaine, freebase and Crack.

3. A method for treating drug abuse in patients taking a drug which causes pharmacologically-induced kindling, which method comprises orally administering to a patient in need an effective amount of carbamazepine or a pharmaceutically acceptable acid addition salt thereof.

4. A method for reducing the craving for cocaine in living animals in need thereof which method comprises orally administering thereto an effective amount of carbamazepine or a pharmaceutically acceptable acid addition salt thereof.

5. A method for reducing the craving for cocaine in humans in need thereof which method includes the step of orally administering daily thereto between about 100 and about 1600 mg carbamazepine or a pharmaceutically acceptable acid addition salt thereof.

6. The method of claim 5 wherein said human is initially given carbamazepine or a pharmaceutically acceptable acid addition salt thereof in a 100 to 200 mg dosage which progressively increases until craving is eliminated to a maximum of about 1600 mg per day.

7. A method for treating cocaine addiction in man by reducing the craving for cocaine, the method including the step of ingesting carbamazepine or a pharmaceutically acceptable acid addition salt thereof in an initial 200 mg dosage followed by progressive increases until cocaine use is controlled, up to a maximum of about 1600 mg per day.

* * * * *

UNITED STATES PATENT AND TRADEMARK OFFICE
CERTIFICATE OF CORRECTION

PATENT NO. : 5,028,611

DATED : July 2, 1991

INVENTOR(S) : Halikas, James A

It is certified that error appears in the above-identified patent and that said Letters Patent is hereby corrected as shown below:

Col. 5, line 27, delete "arbamazepine" and insert

-- carbamazepine --

Signed and Sealed this

Twenty-eighth Day of April, 1992

Attest:

HARRY F. MANBECK, JR.

*Attesting Officer*      *Commissioner of Patents and Trademarks*